United States Patent [19]

Wall et al.

[11] Patent Number: 5,020,376

[45] Date of Patent: Jun. 4, 1991

[54] MICROENVIRONMENTAL SENSORS

[75] Inventors: Peter Wall, Wyndham; Robert S. Pickard, Cardiff; Graham Ensell, Salisbury; David Leong, Southampton, all of United Kingdom

[73] Assignee: University College Cardiff Consultants Limited, Cardiff, United Kingdom

[21] Appl. No.: 149,847

[22] Filed: Jan. 29, 1988

[30] Foreign Application Priority Data

Jan. 30, 1987 [GB] United Kingdom ............. 8702066
Dec. 1, 1987 [GB] United Kingdom ............. 8728102

[51] Int. Cl.$^5$ .................... G01R 3/00; H01L 21/306
[52] U.S. Cl. ................... 73/866.5; 73/DIG. 4; 29/595; 156/647; 156/662
[58] Field of Search ............ 73/866.5, DIG. 4, 432.1; 29/595, 825; 156/625, 647, 662

[56] References Cited

U.S. PATENT DOCUMENTS

| | | | |
|---|---|---|---|
| 4,129,042 | 12/1978 | Rosvold | 73/727 |
| 4,312,115 | 1/1982 | Diedrich et al. | 29/572 |
| 4,682,503 | 7/1987 | Higoshi et al. | 73/755 |
| 4,766,666 | 8/1988 | Sugiyama et al. | 73/727 X |
| 4,790,192 | 12/1988 | Knecht et al. | 73/DIG. 4 |
| 4,793,194 | 12/1988 | Wilner | 73/DIG. 4 |
| 4,872,945 | 10/1989 | Myers et al. | 29/595 X |
| 4,915,778 | 4/1990 | Porth et al. | 156/647 X |

FOREIGN PATENT DOCUMENTS 982174 2/1965 United Kingdom .
1014717 12/1965 United Kingdom .
1251692 10/1971 United Kingdom .

*Primary Examiner*—Tom Noland
*Attorney, Agent, or Firm*—Weingarten, Schurgin, Gagnebin & Hayes

[57] ABSTRACT

A method of making a microenvironmental sensor for neurological use in which the sensor is formed on a silicon wafer by the use of known integrated circuit techniques. A mask is applied to define the outline of the sensor, trenches are etched surrounding the sensor by the use of an anisotropic etchant and the sensor is separated by etching surplus silicon from the rear surface of the wafer.

16 Claims, 3 Drawing Sheets

Shank a b c d

MICROENVIRONMENTAL SENSORS

FIELD OF THE INVENTION

The invention relates to microenvironmental sensors, that is sensors for use in sensing environments of dimensions of the order of $10^{-3}$–$10^{-7}$ meters.

BACKGROUND OF THE INVENTION

A microenvironmental sensor may be in the form of a probe carrying a single sensing interface or an array of such interfaces, each interface being of micro dimensions and mounted on a substrate of the probe, the substrate having micro transverse dimensions. Typically the interface is carried on a shank portion of the probe. Such a probe is used in conjunction with signal processing circuitry.

A typical application of microenvironmental sensors is in physiological work in which it is frequently necessary to use biosensors of extremely small physical dimensions. For example, it may be desired to sense neurological changes of electrical potential by implanting a sensing interface in a single nerve cell with minimal damage to and effect on the surrounding tissue and environment.

Conventional microenvironmental sensors are large, they have substrates of more than 100$\mu$ wide, 25-30$\mu$ thick and sensing interfaces of dimensions more than about 10$\mu$. These suffer from the disadvantages of disturbing and often irreversibly modifying the microenvironment into which they are placed, especially of the microenvironment around the sensing interfaces.

SUMMARY OF THE INVENTION

An object of the present invention is to overcome this problem by providing a method of making a microenvironmental sensor of very small dimensions.

According to the invention there is provided a method of making a microenvironmental sensor from a substrate having a crystalline structure, the method comprising applying sensor means to the substrate surface, anisotropically etching around the sensor means in accordance with the crystal orientation, to produce a required thickness of sensor, and releasing the sensor from the substrate.

The present invention employs substrates of crystalline materials that can be etched by an etchant compatible with the material and acting anisotropically so as to etch the crystal preferentially in a certain crystallographic direction.

Sensors made in accordance with this invention can be made precisely to dimensions of the order of $10^{-3}$–$10^{-7}$ meters. They may have substrates at least a portion of which is of reduced width, typically less than 100$\mu$, and reduced thickness, typically less than 20$\mu$, and sensing interfaces thereon of reduced size, typically less than 5$\mu$. This is especially advantageous for sensors to be used in microenvironments, especially delicate situations in which damage to and effect on the surroundings of the sensor, especially the sensing interface, must be minimised, such as in testing a physiological environment such as human, animal or plant tissue and cells. Other environments which may be tested are soils or metals.

The preferred substrate material is silicon. Other materials which may be used are for example other group 4 elements such as germanium.

The sensor of the invention may be fixed to a carrier which incorporates any required signal processing circuitry. Alternatively, the sensor itself may include signal processing circuitry.

The sensor means preferably comprises conductive means such as metal or polysilicon. Preferred metals are tantalum, titanium, gold, silver, platinum, iridium, aluminium, nickel, rhodium. The conductive means may be insulated from the substrate, preferably by silicon dioxide and/or silicon nitride.

BRIEF DESCRIPTION OF THE DRAWING

A microenvironmental sensor according to the invention will be described in detail with reference to the following drawings, in which.

DESCRIPTION OF THE PREFERRED EMBODIMENT(S)

Figure 1:
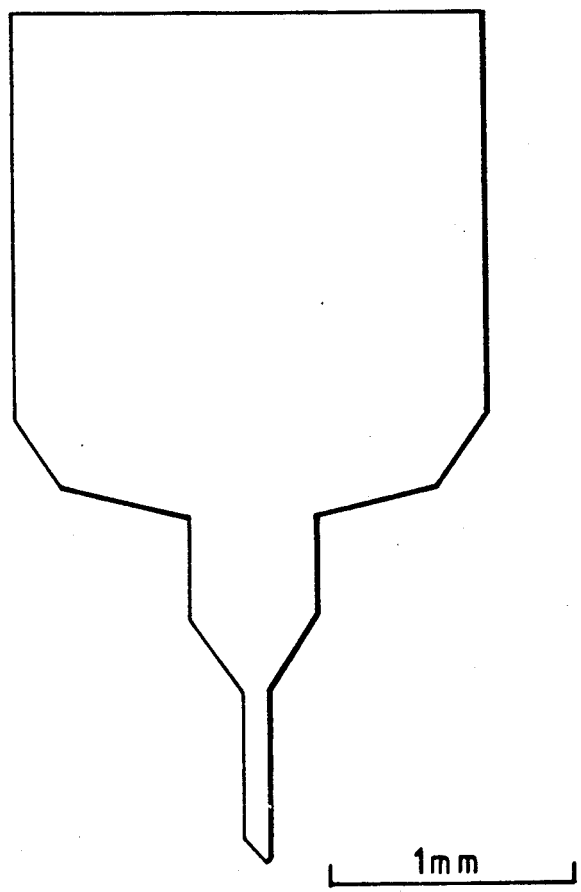
FIG. 1 is a plan view in outline of a sensor produced according to the invention.
Figure 2:
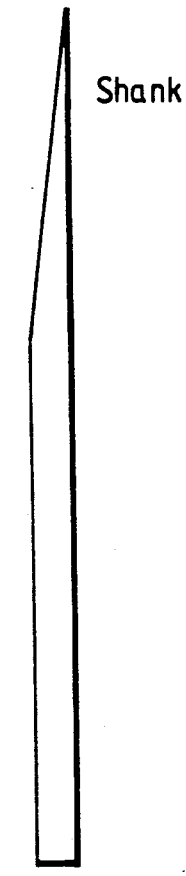
FIG. 2 is a side view of the shank of the sensor.

Referring first to FIG. 1, a sensor consists of a silicon base forming an approximately square body of about 2 mm side from which projects a shank about 700 micrometers in length, 100 micrometers wide and 15 micrometers in depth, tapering to a sharp edge at its extremity as is shown in the side view of FIG. 2.

Figure 3:
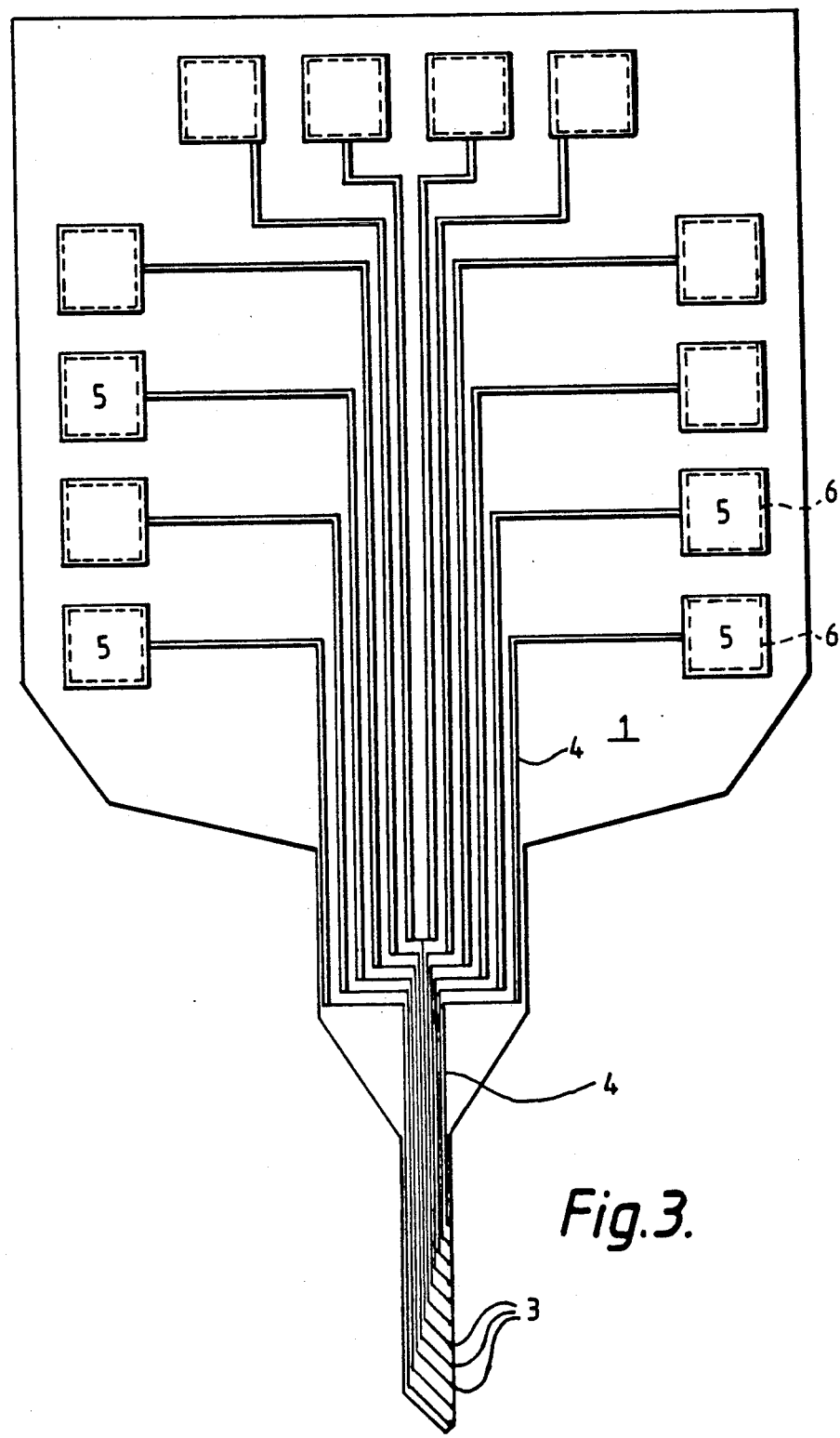
FIG. 3 is a surface view of the sensor showing an array of sensor interfaces, conductors and contact pads before the application of a final insulating and protective layer.

FIG. 3 shows the arrangement of conductors in the sensor. The shank 2 is provided along one edge with a row of twelve sensor interfaces 3 at 50 $\mu$m intervals and each interface is connected by a separate conductor 4 to a respective contact pad 5. Each interface is of dimensions in the range 1-2$\mu$. The view in FIG. 3 is taken before the final stage of manufacture which comprises coating the conductors and the surface of the body with an insulating and protective layer leaving exposed only the sensor interfaces 3 at the very edge of the shank of the sensor and a window over each of the contact areas 5 indicated by the dotted outlines 6.

Figure 4:
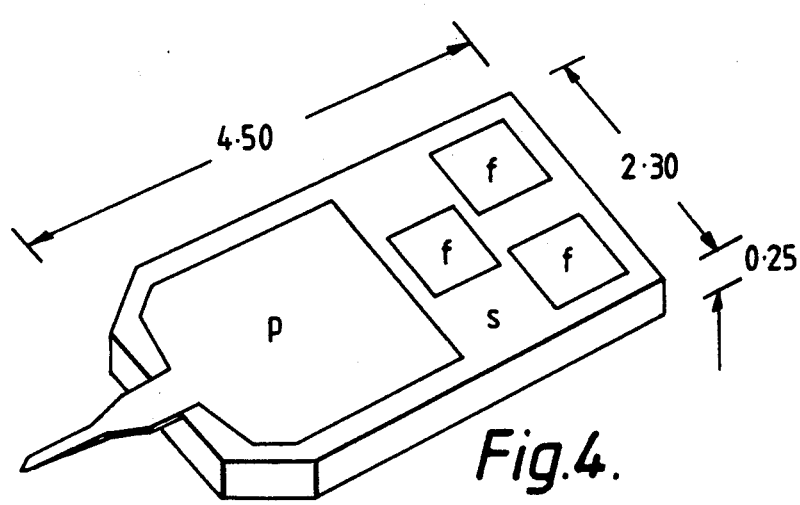
FIG. 4 shows a probe mounted in a carrier with three four channel amplifiers.

When the manufacture of the sensor has been thus completed it is fitted face down into a carrier as shown in FIG. 4, the carrier making contact with the twelve contact pads and connecting them to the inputs of three four-channel amplifiers f mounted in the carrier. The overall dimensions of the carrier are approximately 4.5 mm long, 2.3 mm wide and 0.25 mm thick. The carrier may incorporate any required signal processing circuitry.

The sensor is made from a silicon wafer as follows.

A pattern of conductors corresponding to a sensor corresponding to the arrangement shown in FIG. 3, is formed on one surface of a silicon wafer, which may be a single crystal, by use of known techniques employed in the manufacture of integrated circuits. For example, the conductors may be laid down by vacuum deposition, sputtering or selective etching of a uniformly applied metal layer. The conductors are insulated from the silicon substrate, for example by silicon dioxide. The metal of the sensor interface must not react with the constituents of living cells. A preferred metal is gold, which is biocompatible, chemically stable and not prone to oxidation. The gold is adhered to the conductor via a layer of chrome. The conductors of the sensor are finally protected by an insulating and protective layer, as already described with reference to FIG. 3.

When the conductors and insulators of the sensor have been formed in this way or prior to this, a layer of photoresist is applied to the surface of the silicon wafer and exposed through a mask so as to define the outlines of the sensor as shown in FIG. 1. Then the unexposed portions of the photoresist are dissolved away.

Further lithography is used to mask the conductors and the unmasked surface of the wafer is etched with an etchant which has a strongly preferred direction of action along a particular crystallographic axis. Such a highly anisotropic etchant may consist, for example, of ethylene diamine, pyrocatechol and water. By the use of this etchant the unmasked silicon surrounding the probes is etched away, leaving the sensors upstanding as mesas above the surrounding surface.

The photoresist is then removed with a suitable solvent from the surface of the upstanding sensor and this surface of the wafer is attached with black wax to a teflon paddle. The wafer mounted on its paddle is then immersed into an isotropic further etchant solution which etches away the silicon from the rear until the sensor is separated from the wafer, remaining fixed by the wax to the teflon paddle. In the final stage of the manufacture, the sensor is removed by dissolving the wax with an appropriate solvent.

Figure 5:
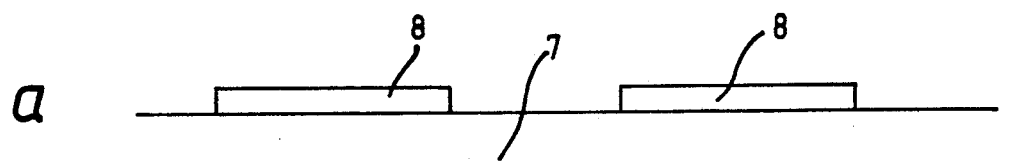
FIGS. 5a-5d comprise diagrams showing successive stages in the making of a probe according to the invention.
Figure 5:
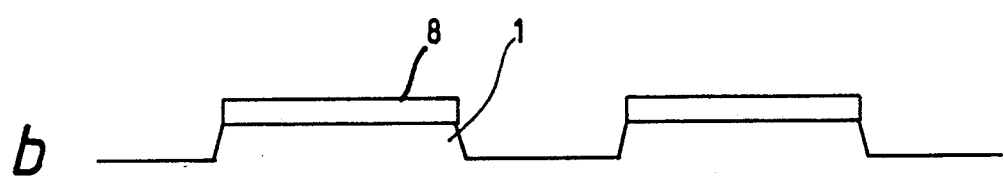
Figure 5:
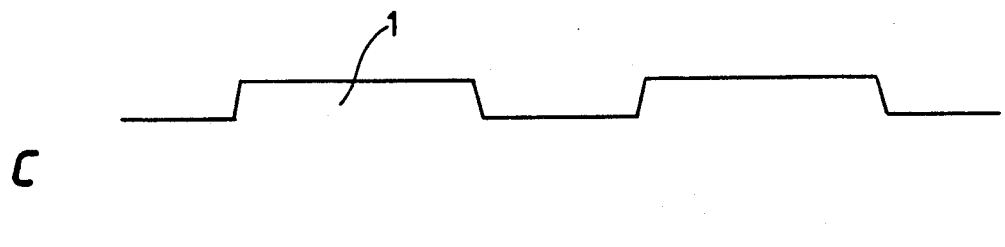
Figure 5:
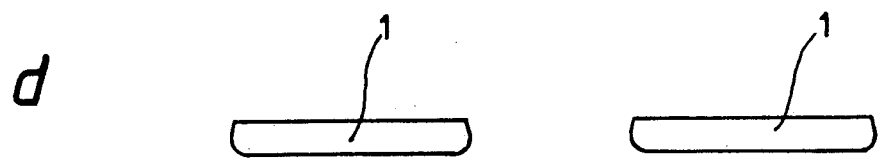

The final etching stages are shown diagrammatically in FIGS. 5a-5d. In FIG. 5a the silicon wafer 7 carries the sensors, each of which is protected by a layer of hardened photoresist 8. FIG. 5b shows the same wafer section after it has been etched from the front surface by the anisotropic etchant, leaving the sensor upstanding as a mesa with its protective layer of photoresist, above the general level of the front surface of the wafer. FIG. 5c shows the section of the wafer with the resist removed, and FIG. 5d shows the separated sensor after the wafer has been eteched away from the rear surface by the final etch, which is isotropic.

More than one sensor may be made from a single wafer as shown in FIGS. 5a-5d.

The sensing interfaces employed in this invention may be in the form of simple electrodes or they may incorporate various interfacing materials to produce various functions. They may comprise thermocouples of dissimilar metals for example.

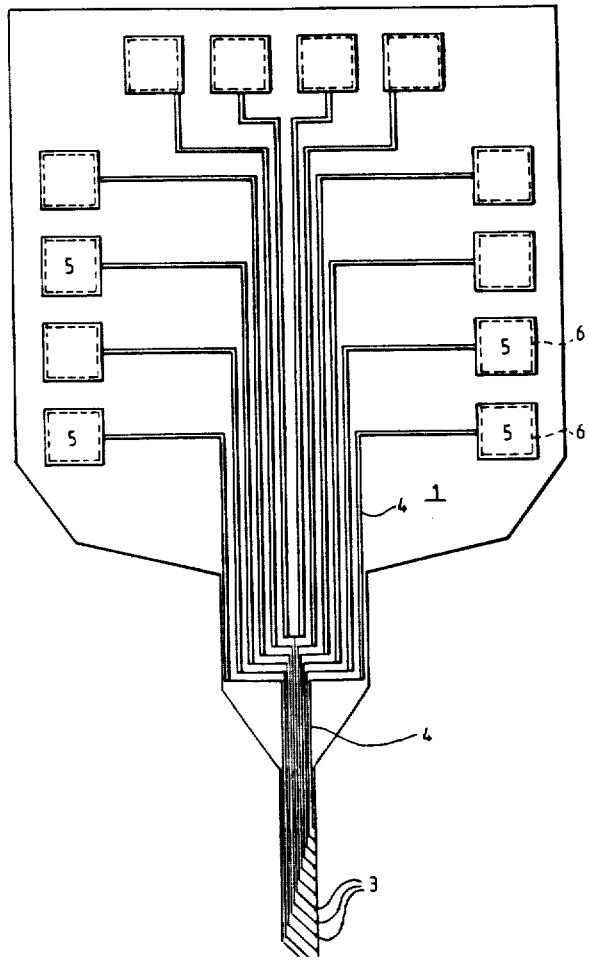

We claim:

1. A method of making a microenvironmental sensor comprising a substrate having a crystalline structure and a crystal orientation, the method comprising applying sensor means to the substrate surface, anisotropically etching around the sensor means in accordance with the crystal orientation, to produce a required thickness of sensor, and releasing the sensor from the substrate.

2. A method according to claim 1, wherein the sensor means is applied by forming a conductive pattern corresponding to the sensor on the surface of the substrate.

3. A method according to claim 2, in which the conductor pattern on the sensor includes an array of sensor interfaces each individually connected to a separate contact pad.

4. A method according to claim 1, comprising forming an etch-resistant mask on the surface defining the outline of the sensor prior to the anisotropic etch.

5. A method according to claim 1, comprising masking the anisotropically etched surface and etching the opposite surface of the substrate until the sensor has been separated therefrom.

6. A method according to claim 5, in which the anisotropic etchant comprises ethylene diamine, pyrocatechol and water.

7. A method according to claim 5, in which the final masking of the etched substrate surface is achieved by waxing the surface to a paddle.

8. A method according to claim 1, in which the substrate is of silicon.

9. A method according to claim 1, wherein the sensor is released from the substrate by an isotropic etch.

10. A method according to claim 1 of making a microenvironmental sensor at least a portion of which is in one dimension 10–20$\mu$, which bears sensor means of dimensions 1–10$\mu$.

11. Use of a sensor made according to claim 1, in sensing properties of an environment of dimensions of the order of $10^{-3}$–$10^{-6}$ meters.

12. Use according to claim 11, wherein the dimensions of the environment are of the order of $10^{-3}$–$10^{-7}$ meters.

13. The method of making a microenvironmental sensor of claim 1 comprising a silicon substrate having a crystalline structure, the method comprising:
   forming a conductive pattern corresponding to the sensor on the surface of the substrate to apply the sensor means;
   forming an etch-resistant mask on the surface defining the outline of the sensor prior to the anisotropic etch;
   masking the anisotropically etched surface and etching the opposite surface of the substrate until the sensor has been separated therefrom;
   said conductor pattern on said sensor including an array of sensor interfaces each individually connected to a separate contact pad;
   producing said anisotropic etch with ethylene diamine, pyrocatechol and water;
   releasing the sensor from the substrate with an isotropic etch;
   making a final masking of the substrate surface by waxing the surface to a paddle; and
   making said microenvironmental sensor having at least a portion of which is in one dimension 10–20$\mu$, and having the sensor means of dimensions 1–10$\mu$.

14. Use of a sensor made according to claim 13, in sensing properties of an environment of dimensions of the order of $10^{-3}$–$10^{-6}$ meters.

15. Use of a sensor according to claim 14, wherein the dimensions of the environment are of the order of $10^{-3}$—$10^{-7}$ meters.

16. A microenvironmental sensor comprising a crystalline substrate released by a combination of anisotropic and isotropic etching from a crystalline material, and sensing interface means on the surface of at least a portion of the substrate, wherein one dimension of the portion of the substrate is 10–20$\mu$ and the sensor means is of dimensions 1–10$\mu$.

* * * * *

UNITED STATES PATENT AND TRADEMARK OFFICE
CERTIFICATE OF CORRECTION

PATENT NO. : 5,020,376

DATED : June 4, 1991

INVENTOR(S) : Peter Wall, et al

It is certified that error appears in the above-identified patent and that said Letters Patent is hereby corrected as shown below:

The title page, should be deleted to be replaced with the attached title page.

Title page, item [73] Assignee: should read --University College Cardiff Consultants Limited, Cardiff, United Kingdom and University of Southhampton, Southhampton, United Kingdom--.

Signed and Sealed this

Eleventh Day of May, 1993

Attest:

MICHAEL K. KIRK

Attesting Officer

Acting Commissioner of Patents and Trademarks

United States Patent [19]
Wall et al.

[11] Patent Number: 5,020,376
[45] Date of Patent: Jun. 4, 1991

[54] MICROENVIRONMENTAL SENSORS

[75] Inventors: Peter Wall, Wyndham; Robert S. Pickard, Cardiff; Graham Ensell, Salisbury; David Leong, Southampton, all of United Kingdom

[73] Assignee: University College Cardiff Consultants Limited, Cardiff, United Kingdom

[21] Appl. No.: 149,847

[22] Filed: Jan. 29, 1988

[30] Foreign Application Priority Data

Jan. 30, 1987 [GB] United Kingdom ................. 8702066
Dec. 1, 1987 [GB] United Kingdom ................. 8728102

[51] Int. Cl.$^5$ ...................... G01R 3/00; H01L 21/306
[52] U.S. Cl. .............................. 73/866.5; 73/DIG. 4; 29/595; 156/647; 156/662
[58] Field of Search ............. 73/866.5, DIG. 4, 432.1; 29/595, 825; 156/625, 647, 662

[56] References Cited

U.S. PATENT DOCUMENTS

| | | | |
|---|---|---|---|
| 4,129,042 | 12/1978 | Rosvold | 73/727 |
| 4,312,115 | 1/1982 | Diedrich et al. | 29/572 |
| 4,682,503 | 7/1987 | Higoshi et al. | 73/755 |
| 4,766,666 | 8/1988 | Sugiyama et al. | 73/727 X |
| 4,790,192 | 12/1988 | Knecht et al. | 73/DIG. 4 |
| 4,793,194 | 12/1988 | Wilner | 73/DIG. 4 |
| 4,872,945 | 10/1989 | Myers et al. | 29/595 X |
| 4,915,778 | 4/1990 | Porth et al. | 156/647 X |

FOREIGN PATENT DOCUMENTS

| | | |
|---|---|---|
| 982174 | 2/1965 | United Kingdom . |
| 1014717 | 12/1965 | United Kingdom . |
| 1251692 | 10/1971 | United Kingdom . |

Primary Examiner—Tom Noland
Attorney, Agent, or Firm—Weingarten, Schurgin, Gagnebin & Hayes

[57] ABSTRACT

A method of making a microenvironmental sensor for neurological use in which the sensor is formed on a silicon wafer by the use of known integrated circuit techniques. A mask is applied to define the outline of the sensor, trenches are etched surrounding the sensor by the use of an anisotropic etchant and the sensor is separated by etching surplus silicon from the rear surface of the wafer.

16 Claims, 3 Drawing Sheets